US00PP28635P2

(12) United States Plant Patent
Hansen

(10) Patent No.: US PP28,635 P2
(45) Date of Patent: Nov. 14, 2017

(54) ***DIANTHUS* PLANT NAMED 'SPIKED PUNCH'**

(50) Latin Name: ***Dianthus* hybrid**
Varietal Denomination: Spiked Punch

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/330,910

(22) Filed: Nov. 14, 2016

(51) Int. Cl.
*A01H 5/02* (2006.01)

(52) U.S. Cl.
USPC ..... Plt./277

(58) Field of Classification Search
USPC ..... Plt./277
CPC ..... A01H 5/0233
See application file for complete search history.

*Primary Examiner* — Kent L Bell

(57) ABSTRACT

A new and unique cultivar of perennial carnation or pinks, *Dianthus* plant named 'Spiked Punch' with numerous, large, fully-double, fragrant flowers, on well-branched stems having up to 6 flowers per stem. Petals are fuchsia pink with darker red-purple band and deeply incised margins and apices. Plant has vigorous compact habit with thin, finely textured, gray-green foliage. *Dianthus* 'Spiked Punch'.

1 Drawing Sheet

Botanical denomination: *Dianthus* hybrid.
Cultivar designation: 'Spiked Punch'.

BACKGROUND OF THE INVENTION

The present invention relates to the new and distinct cultivar of carnation or pinks from the genus *Dianthus* and given the cultivar name 'Spiked Punch' previously known only internally by the breeder code 11-75-01. The new plant was the result of an intentional cross on May 13, 2011 by the inventor between *Dianthus* 'Starlette' U.S. Plant Pat. No. 21,438 as the female or seed parent and 'Devon Flavia' U.S. Plant Pat. No. 15,903 as the male or pollen parent. The cross was harvested Jun. 16, 2011. The new hybrid was first isolated from trials at a wholesale perennial nursery in Zeeland, Mich. during the summer of 2012 as a single seedling and given the breeder number 11-75-01 during the remaining evaluation processes. *Dianthus* 'Spiked Punch' has been asexually propagated at the same nursery in Zeeland, Mich. since 2012 using traditional shoot tip cutting procedures and found to reproduce plants that are identical and exhibit all the characteristics of the original plant.

No plants of *Dianthus* 'Spiked Punch' have been sold in this country, or anywhere in the world, prior to the filing of this application, nor has any disclosure of the new plant been made prior to the filing of this application with the exception of that which was disclosed within one year of the filing of this application and was either derived directly or indirectly from the inventor.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant.

Compared to the new plant, the female parent, 'Starlette', the new plant has a higher petal number per flower, larger flowers with more petals, and the petal color is deeper red-purple than deep raspberry pink. Compared to the male parent, 'Devon Flavia', the new plant has a higher petal number per flower, broader flowers, deeper incised petals and deeper petal color hot magenta pink rather than the lighter pink of 'Devon Flavia'.

Other similar *Dianthus* include: 'Pomegranate Kiss' U.S. Plant Pat. No. 21,895, 'Black Cherry Wild' U.S. Plant Pat. No. 21,893, and 'Cranberry Cocktail' U.S. Plant patent application Ser. No. 14/998,557. Compared to 'Pomegranate Kiss' the new plant is taller in habit, has more petals per flower and does not have the lighter splashing or petal margin and the hue is closer to purple. Compared to 'Black Cherry Wild' the new plant is slightly taller in habit, has more petals per flower, the petals do not have the white edge and the petal hue is more purple and less red. Compared to 'Cranberry Cocktail' the new plant is shorter in habit, petals have deeper marginal incision, petals have the dark band on the limb and the main hue is closer to purple and less red.

*Dianthus* 'Spiked Punch' is distinct from its parents and all other *Dianthus* known to the applicant in the following combined traits:

1. Fully-double flowers with numerous petals of fuchsia pink with darker red purple band.
2. Petals having a deeply serrated or incised apex and margin.
3. Numerous flowers per peduncle with many flowers on heavily branched stems.
4. Large flower size producing a sweetly spicy fragrance.
5. No vernalization required for flower production.
6. Floriferous, vigorous, with compact habit and finely-textured gray-green foliage

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
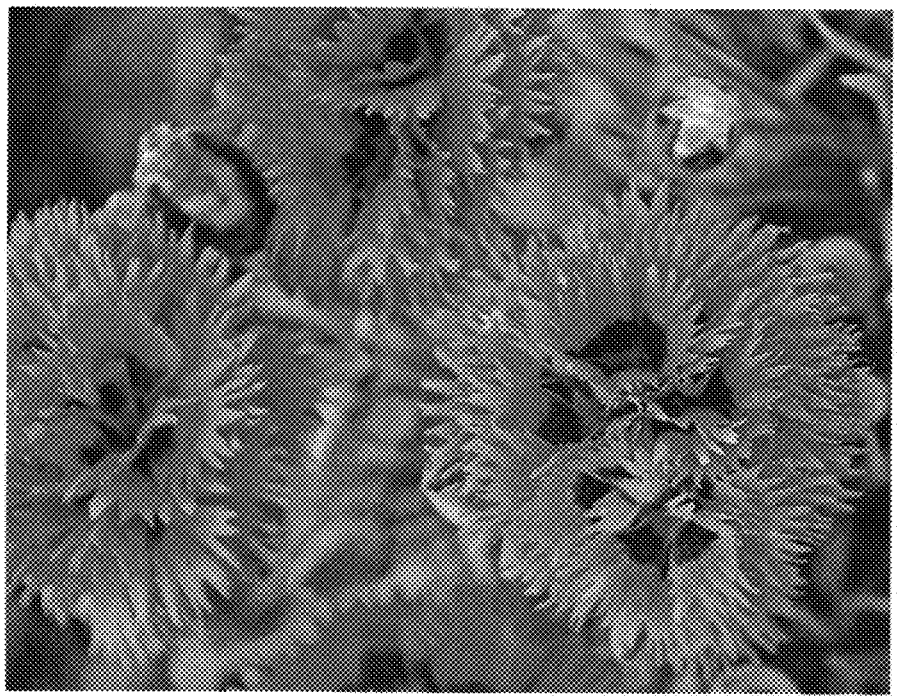
FIG. 1 shows a close-up of the flowers and buds.
Figure 2:
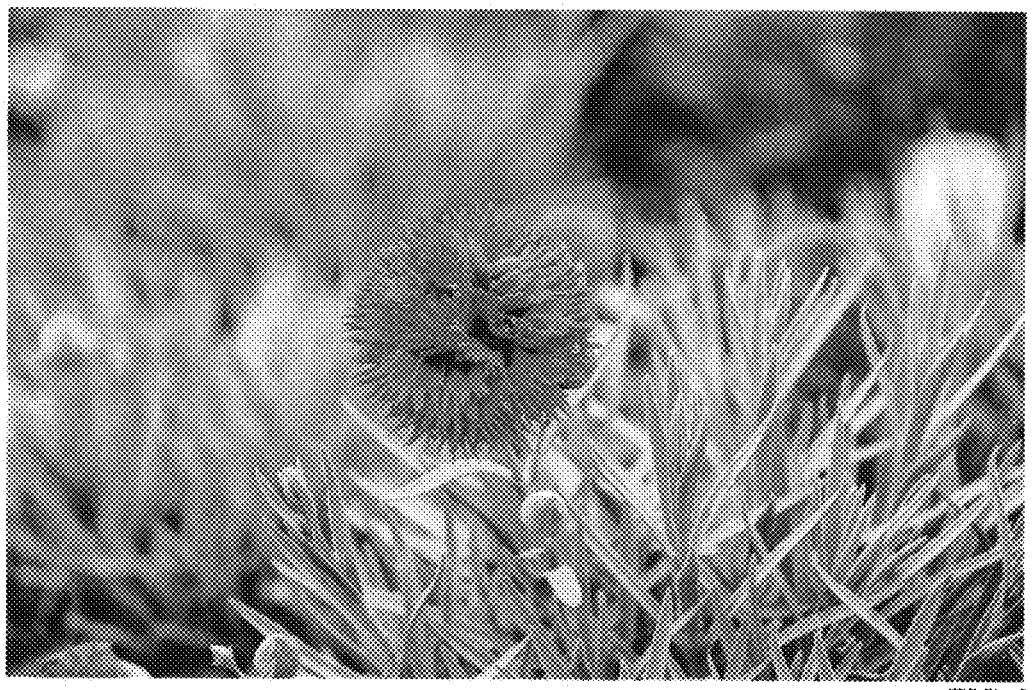
FIG. 2 shows the habit of the plant in mid-season flowering.

The following detailed description of the new plant is based on observations of one-year-old plants in greenhouse-grown containers at a nursery in Zeeland, Mich. as well as two-year-old plants in a full-sun trial garden location in Zeeland, Mich. with supplemental watering, minimal addition of fertilizer and free of other plant growth regulators. All color usage is in accordance with the 2001 edition of The Royal Horticultural Colour Chart except where common dictionary terms are used.

Botanical classification: *Dianthus* hybrid.

Parentage: 'Starlette' U.S. Plant Pat. No. 21,438 as the female or seed parent and 'Devon Flavia' U.S. Plant Pat. No. 15,903 as the male or pollen parent.

Plant habit: Caespitose, herbaceous, evergreen perennial; stems and peduncles branched, erect to arching with weight, number and size of flowers; height of foliage about 8.5 cm and about 30.0 cm across; height in flower is about 16.5 cm.

Root system: Fine, fibrous; color nearest RHS 155D.

Vigor: Good, spring planted plugs finish in 3.8 liter pots in seven to eight weeks.

Foliage:

*Leaf type*.—Simple; linear; opposite; decussate; sessile; glabrous, glaucous on adaxial and abaxial; to microscopically serrulate; acute apex; base decurrent, adpressed along stem; no fragrance detected.

*Leaf dimensions*.—To about 5.0 cm long and about 2.0 mm wide, average about 4.2 cm long and 2.0 mm wide.

*Leaf color in greenhouse*.—Young expanding leaves adaxial between RHS N138B and RHS 122A, abaxial between RHS 138C and RHS 122A; mature adaxial between RHS N138A and RHS 122A, abaxial between RHS N138A and RHS 122A.

*Leaf color in trial garden*.—Young and mature leaves adaxial between RHS 189A and RHS 189B, abaxial nearest RHS 189B.

*Venation*.—Not pronounced; obscurely pinnate, coloration same as that of leaf.

Stems: Beginning erect and becoming arching with development of flowers; terete, glabrous, glaucous, branching at alternate nodes; about 100 per plant.

*Stem size*.—About 8.5 cm long and about 3.0 mm wide at base.

*Stem color*.—Nearest RHS N138C.

*Branching*.—Numerous; alternate from upper and lower leaf axils; about 12 per main stem and about 200 per plant; branch length average about 6.5 cm at time of initial flowering.

*Nodes*.—About 17 per stem; about 3.0 mm across; color nearest RHS N187D.

*Internodes*.—Average about 1.1 cm apart depending on growing temperature, shorter in cooler conditions.

Inflorescence:

*Type*.—Terminal, cymose; salverform; actinomophic; completely double.

*Attitude*.—Upright to slightly arching.

*Dimension*.—About 4.5 cm across and extending about 32.0 mm above calyx tube base.

*Flowers per stem*.—Typically four to six.

*Pedicel*.—Glaucous, glabrous, terete.

*Pedicel size*.—Terminal flower about 20.0 mm long and about 2.0 mm diameter; other flowers average about 15.0 mm long and 1.5 mm diameter.

*Pedicel color*.—Nearest RHS 189B.

*Flower bud one day prior to opening*.—Glaucous, glabrous, ellipsoid with rounded apex and rounded base.

*Flower bud size*.—One day prior to opening — about 2.8 cm long and about 1.3 cm wide.

*Flower bud color*.—With petals exposed and still tight — petals nearest RHS 71B at apex and between sepal teeth nearest RHS 155D.

*Flower period*.—Beginning late spring and repeating in early fall; effective about four weeks per flowering season.

*Flower fragrance*.—Light, sweet spicy, clove-like.

*Flower lasting quality*.—About ten days on or cut from plant.

*Petals*.—Glabrous; about 50 per flower, with as many as eight petals split in the distal portion of the claw and the limb; consisting of a rounded blade or limb and a claw, outer petals with broader and more rounded limb; limb obovate with long tapered claw apex with coarse dentations 5.0 mm deep; limb bent slightly outwardly in distal 16.0 mm; about 1.0 mm across; persistent.

*Petal color greenhouse grown*.—Adaxial claw base nearest RHS 145D, mid-claw nearest RHS 145B, distal claw nearest RHS N78C, limb base (dark band) between RHS N79B and RHS N79C; abaxial claw base nearest RHS 150D, mid-claw nearest RHS 145B, distal claw nearest RHS 77D, limb nearest RHS 78C.

*Petal color outdoor grown*.—Adaxial claw nearest RHS 145D, mid-claw nearest RHS 145B, distal claw nearest N78C, limb base nearest blend of RHS 71A and RHS N79A; abaxial claw base nearest RHS 145C, mid-claw nearest RHS 145B, distal claw nearest RHS 77D, limb between RHS 71B and RHS 71C.

*Petal dimension*.—Size to about 32.0 mm long and 20.0 mm across at widest part of limb, average about 30.0 mm long and about 15.0 mm wide; claw portion average about 15.0 mm long and about 1.0 mm at base; limb portion average about 15.0 mm long and 15.0 mm wide.

*Androecium*.—Not produced or up to two rudimentary; fused basal phalange. Filament: average total size 9.0 mm long and 0.3 mm diameter; color nearest RHS 155D. Anther: absent or rudimentary; flattened ellipsoid; to 0.5 mm long and 0.4 mm across; color nearest RHS 158A. Pollen, not observed.

*Gynoecium*.—Single, split. Style: erect then curling 360 degrees in distal 3.0 mm; terete. Pistil: glabrous abaxial surface and puberulent adaxial surface; irregularly curled; average about 20.0 mm long and 0.6 mm diameter; color abaxial basal one-half whiter than RHS 155D, abaxial distal one-half and adaxial nearest RHS 79B. Stigma: puberulent; about 0.5 mm long and 0.5 mm wide; color nearest RHS 79A.

Ovary: superior; ellipsoid-shaped; about 7.0 mm long and 3.5 mm wide; color distally nearest RHS 150C and proximally nearest RHS 150D.

*Calyx*.—Glabrous, glaucous; margins entire; form; five-toothed corolla tube fused in proximal 1.0 cm; individually about 1.7 cm long and about 0.6 cm across; campanulate to about 17.0 mm long and about 11.0 mm in diameter.

*Calyx color*.—Abaxial nearest RHS 138B with heavy blushing of nearest RHS 187A toward apex; adaxial nearest RHS 138B.

*Peduncle*.—Glabrous, glaucous, terete, about 6.5 cm long and about 2.5 mm diameter at base.

*Peduncle color*.—Nearest RHS N138C.

*Pedicel*.—Of main flower about 1.8 cm long and 1.0 mm diameter.

*Pedicel color*.—Nearest RHS N138C.

*Bracts*.—Two pair, opposite, glaucous, glabrous; sessile margin entire, broadly obtuse to deltoid with broadly acute apex; outer pair about 10.0 mm long and about 3.0 mm wide, inner pair about 7.0 mm long and 4.0 mm wide.

*Bract color*.—Each pair identical, abaxial and adaxial center nearest RHS 137A and margins nearest RHS 145C to slightly translucent, abaxial tinted with RHS 187C.

Fruit: Capsule; ovoid to cylindrical; opening by 4 teeth; about 3.5 mm long and 2.0 mm diameter; color between RHS 164B and RHS 165C when dried.

Seed: Not observed.

Disease resistance: The new plant is resistance to center die out from fungus or high temperatures. The plant grows best with adequate moisture and well-drained soil, but is able to tolerate some drought once established. Hardiness at least from USDA zone 4 through zone 9.

It is claimed:

1. A new and distinct *Dianthus* plant named 'Spiked Punch' essentially as herein described and illustrated.

* * * * *